(12) United States Patent
Banjanin

(10) Patent No.: US 6,423,006 B1
(45) Date of Patent: Jul. 23, 2002

(54) METHOD AND APPARATUS FOR AUTOMATIC VESSEL TRACKING IN ULTRASOUND SYSTEMS

(75) Inventor: Zoran Banjanin, Newcastle, WA (US)

(73) Assignee: Siemens Medical Solutions USA, Inc., Iselin, NJ (US)

( * ) Notice: Subject to any disclaimer, the term of this patent is extended or adjusted under 35 U.S.C. 154(b) by 0 days.

(21) Appl. No.: 09/489,575

(22) Filed: Jan. 21, 2000

(51) Int. Cl.$^7$ ................................................ A61B 8/00
(52) U.S. Cl. ...................... 600/453; 600/441; 600/455
(58) Field of Search .................................. 600/453–456, 600/440–447; 367/103; 73/633; 342/84, 62

(56) References Cited

U.S. PATENT DOCUMENTS

| | | | | |
|---|---|---|---|---|
| 5,280,787 A | * | 1/1994 | Wilson et al. | 600/456 |
| 5,287,753 A | * | 2/1994 | Routh et al. | 600/454 |
| 5,365,929 A | * | 11/1994 | Peterson | 600/456 |
| 5,429,137 A | * | 7/1995 | Phelps et al. | 600/455 |
| 5,785,655 A | * | 7/1998 | Goodsell, Jr. et al. | 600/441 |

* cited by examiner

*Primary Examiner*—Marvin M. Lateef
*Assistant Examiner*—Ruby Jain

(57) ABSTRACT

A method for automatically placing a range gate over a moving blood vessel during ultrasound imaging. Doppler data received from a number of depths in the tissue is analyzed in order to calculate the average velocity of the tissue at each depth. A search is performed in the average velocities to select a maximum velocity. The maximum velocity is associated with a blood vessel and a range gate is placed at a depth corresponding to the maximum velocity. In a presently preferred embodiment of the invention, the average velocity is calculated by performing a first lag autocorrelation of the echo data received from each depth in response to a series of Doppler pulses.

10 Claims, 2 Drawing Sheets

Average Velocity at Each Depth

Average Velocity at Each Depth

METHOD AND APPARATUS FOR AUTOMATIC VESSEL TRACKING IN ULTRASOUND SYSTEMS

FIELD OF THE INVENTION

The present invention relates to medical imaging systems in general, and in particular, to ultrasound imaging systems.

BACKGROUND OF THE INVENTION

In many clinical applications, a physician or ultrasound sonographer is interested in viewing more than one type of ultrasound data at a time. This is particularly true when diagnosing arterial diseases where the physician wishes to view the structure of a patient's vessel and the velocity or volume of blood flowing through it.

One dual imaging mode is referred to as BD mode, wherein the ultrasound system produces a two-dimensional greyscale image of the tissue structure beneath the ultrasound transducer as well as a spectral Doppler graph showing velocity of moving blood flow at a position in the body defined by a range gate.

A common problem encountered during BD mode imaging occurs when a vessel being viewed moves with the cardiac cycle or due to patient breathing. With the vessel moving, the user has to continually reposition the range gate over the vessel in order to capture the Doppler data of the blood flowing within the vessel. Moving the range gate can be particularly cumbersome for cardiac vessels which are generally small and tend to move relatively large distances with each cardiac cycle.

Given this problem associated with conventional dual mode imaging, there is a need for a mechanism that can automatically track the position of a vessel as it moves with the cardiac cycle or with movement of the patient and can reposition the range gate over the vessel without user intervention.

SUMMARY OF THE INVENTION

The present invention is a method for automatically positioning a range gate over a moving vessel for use in capturing ultrasound data. A sequence of Doppler pulses is applied to a patient and an average velocity of the tissue is determined at a number of depths. A search is performed to locate the depth having the greatest velocity. The range gate is then placed at the depth associated with the greatest velocity.

In a currently preferred embodiment of the invention, the average velocity at each depth is determined using an MC imaging mode that calculates the first lag autocorrelations of the Doppler data received from the sequence of Doppler pulses. The results of the autocorrelation calculations may be interpolated to locate a depth having a peak mean velocity over which the range gate is placed. Preferably, the MC imaging calculations are performed in the background and do not interfere with the normal display data being produced by the ultrasound imaging system

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION OF THE PREFERRED EMBODIMENT

As indicated above, the present invention is a method of automatically tracking a vessel by determining the location of maximum average blood velocity in a tissue sample and placing a range gate at a corresponding depth in the tissue.

Figure 1A:
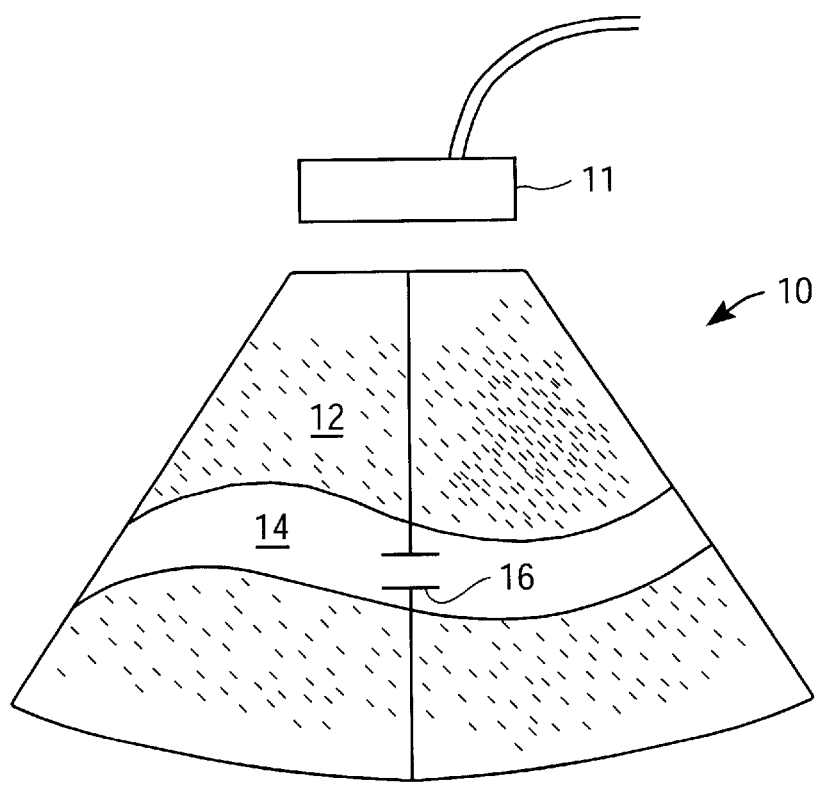
FIG. 1 illustrates a conventional dual mode ultrasound display.
Figure 1B:
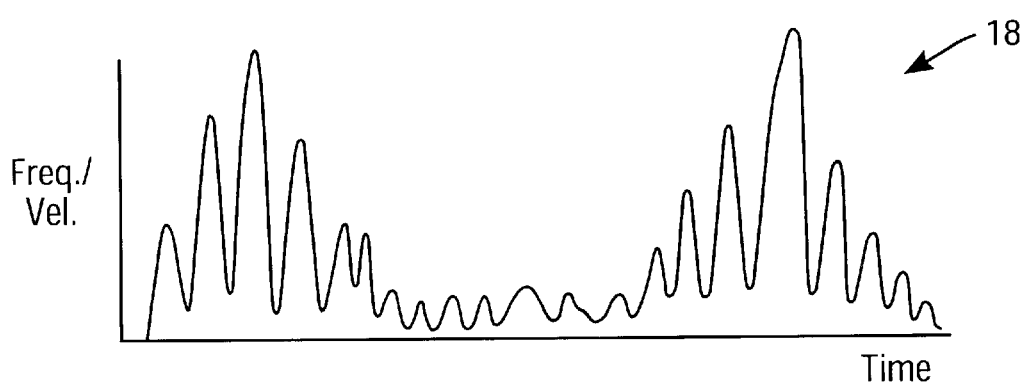

FIG. 1 illustrates a conventional dual mode ultrasound display. The display includes a two-dimensional greyscale image 10 of the tissue 12 that is beneath an ultrasound transducer 11. The tissue may include layers of fat, muscle, bone and one or more blood vessels 14. To determine the rate of blood flow in a vessel 14, a physician or sonographer places a range gate 16 over the blood vessel in the image. The range gate defines the depth at which the echo signals use to calculate blood flow are received. The echo signals that originate in the area of the range gate 16 are used to calculate a spectral Doppler display 18 that shows the physician the velocity of blood flow in the vessel 14. From the greyscale image 10 of the tissue structure plus the spectral Doppler display 18, a physician is able to diagnose the health of the patient's vessel 14.

As indicated above, one of the problems that occurs in conventional dual mode ultrasound imaging systems is the fact that a vessel may move in response to the cardiac cycle breathing or small probe movement. In the past a physician or sonographer had to manually place the range gate 16 over the vessel as it moved in order to properly capture the data for spectral Doppler display. Depending upon the size of the vessel and its amount of movement, the manual placement of the range gate could be time-consuming and distracting.

Figure 2A:
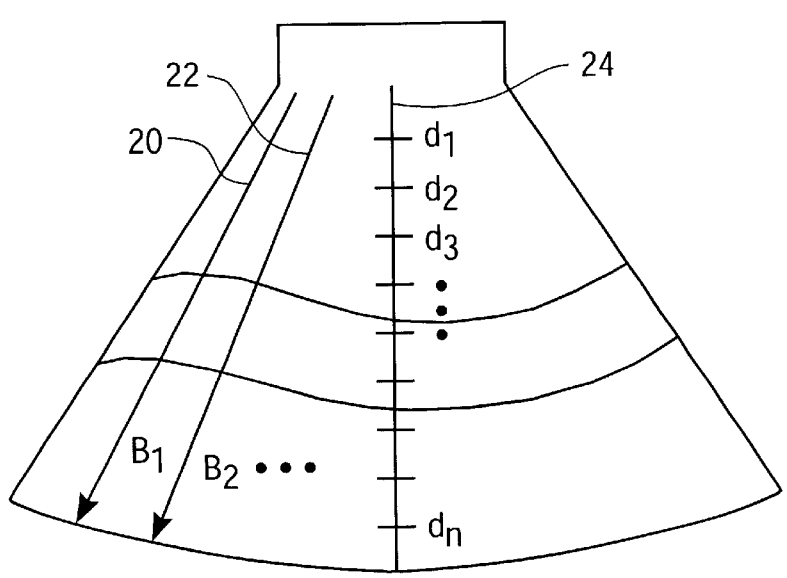
FIG. 2 illustrates a method of automatically tracking a vessel according to the present invention.
Figure 2B:
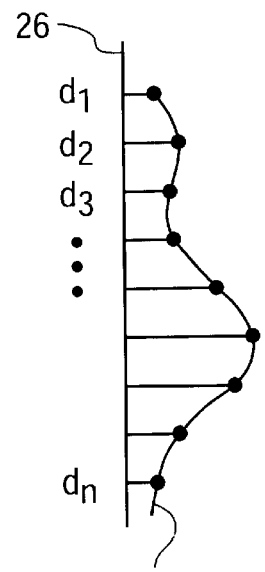

FIG. 2 illustrates a method of tracking a vessel in an image in order to automatically position the range gate over the vessel according to the present invention. The present invention tracks a vessel by searching for a maximum average rate of blood flow in a tissue sample. The ultrasound system alternately transmits brightness mode (13) along a series of beam lines 20, 22 and Doppler (D) ultrasound pulses into the patient. Echo data from the B mode pulses are analyzed in a conventional fashion to produce a two-dimensional greyscale image of the tissue under the transducer.

For the Doppler processing, each of the Doppler pulses is transmitted along the same beam line 24 over which the range gate can be placed. The Doppler echo signals that originate at the depth specified by the range gate are processed to produce the spectral Doppler display in the conventional fashion. To determine where to place the range gate, the length of the Doppler beam line is divided into a number of segments shown as $d_1$–$d_n$, each of which corresponds to a different depth range in the tissue. Each segment is preferably between 1 min and 1 cm long. Doppler echo signals received from each segment are analyzed along with the echo signals created in response to subsequent Doppler pulses in order to determine an average velocity of the tissue at that segment depth. The average velocity versus tissue depth may be stored as a graph 26 in a processor within the ultrasound system. Once the average tissue velocity for each depth is calculated, a search is made to determine the maximum average velocity. To track a vessel, it is assumed that the depth of the maximum velocity corresponds to the location of the vessel. Once the point of maximum velocity has been determined, the range gate is then placed by a central processing unit at that depth.

In the presently preferred embodiment of the invention, the average velocity at each depth is calculated by computing the first lag autocorrelation for Doppler echo signals in response to the sequence of Doppler pulses. The first lag autocorrelation is calculated according to the formula:

$$R_1 = \frac{1}{n}\sum_{k=1}^{n} x^*(k-1) \cdot x(k). \quad (1)$$

where x is the Doppler echo signals received from the same depth in the tissue and k is the number of the echo signals being analyzed. The search for the vessel location may involve interpolating the first lag autocorrelation results if the maximum is not centered over a particular depth where the velocity was calculated. Once the depth of the maximum average velocity has been located, a central processing unit within the ultrasound system places the range gate at that depth that corresponds to the peak velocity.

If the ultrasound transducer is positioned such that two or more vessels are being imaged, the physician or sonographer may be required to manually position the range gate over the particular vessel to be analyzed. In this case, the range of depths in which the search for the maximum average velocity is made can be limited to the range of expected movement of the selected vessel. This range may be marked by a user after observing the vessel for several cardiac cycles. In this manner, the likelihood that the ultrasound system will position the range gate over another vessel is minimized.

Figure 3:
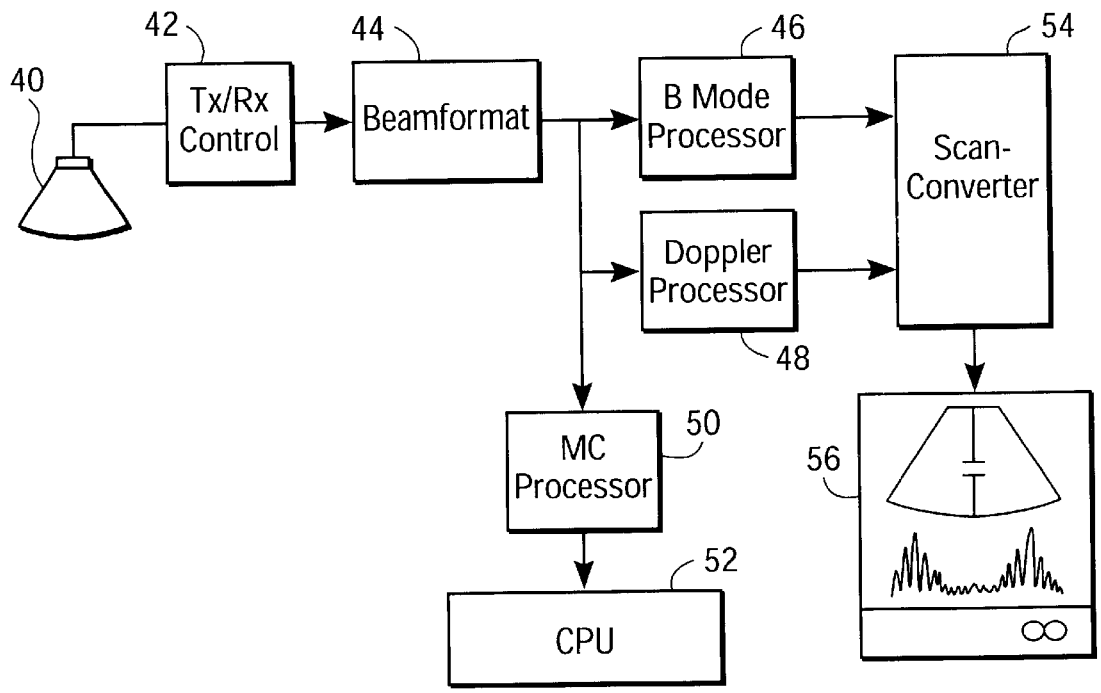
FIG. 3 illustrates an ultrasound system that is programmed to track a vessel according to the present invention.

FIG. 3 illustrates a block diagram of an ultrasound system according to the present invention. A transducer 40 directs the ultrasound pulses into the patient and receives the echo signals generated by the tissue and moving blood flow under the transducer.

Echo signals received by the transducer are applied to a beamformer 44 that focuses the received echo signals. The output of the beamformer 44 is applied to a B-mode processor 46 or a Doppler mode processor 48 depending on the type of echo signals received. The B-mode processor produces a greyscale image of the tissue beneath the transducer 40 in a conventional fashion. The Doppler mode processor 40 analyzes the received Doppler echo signals to produce the spectral Doppler display in a conventional fashion. To calculate the position of a vessel in the tissue, the echo signals produced by the beamformer 44 are also applied to an MC processor 50 that calculates the average velocity of the tissue at each depth as described above. The MC processor preferably operates in the background of the B-mode and Doppler mode processors 46 and 48. The MC processor 50 searches the calculated average velocity values for the maximum average velocity and instructs a central processing unit 52 to move the range gate to a depth that corresponds to the maximum average velocity. The output of the signals of the B-mode and Doppler mode processors 46, 48 are applied to a scan converter 54 that converts the signals into a format that can be displayed on a monitor 56.

The present invention is not limited to tracking vessel movement along a single beam line. For example, it is known that a single transmit pulse can be used to receive echo signals along multiple beam lines. See U.S. Pat. No. 5,544,128 issued to Kim et al. If a broad transmit pulse is used, echo signals received on multiple beam lines can be analyzed for a point of maximum velocity and a CPU instructed to move the range gate to the location that corresponds to the point of maximum velocity. This approach can also be used to track vessel movement in three dimensions by transmitting pulses and receiving echo signals along beam lines that lie in different planes. When receiving echoes along multiple beam lines there is preferably a separate MC processor for each beam line on which echo signals are received.

In addition to using the maximum average velocity to indicate a vessel, the B-mode data can also be used. The B-mode samples in the vessels tend to have smaller amplitudes due to the lack of scatters in the vessel. Therefore, the MC processor may also analyze the B-mode echo signal to search a depth of tissue that exhibits a minimum B-mode echo intensity and a maxi=m average velocity in order to estimate accurate vessel location.

It should also be noted that due to the cardiac cycle, blood flow is more or less pulsatile. This pulsatility has to be taken into account by the CPU during the processing of velocity peak estimation along depth.

As can be seen from the above, the present invention eliminates the need for a physician or a sonographer to maintain the position of a range gate over a vessel in an ultrasound image by tracking the movement of the vessel based on a calculation of the maximum average flow rates in the tissue.

The embodiments of the invention in which an exclusive property or privilege is claimed are defined as follows:

1. A method of tracking a vessel in an ultrasound imaging system, comprising:
   transmitting a series of Doppler ultrasound pulses into a tissue sample;
   receiving echo signals from a number of depths in the tissue sample;
   analyzing the echo signals to determine the average velocity of the tissue at each of the number of depths;
   determining with a processor a first depth of the number of depths in the tissue sample having the highest average velocity;
   determining with a processor a second depth of the number of depths in the tissue sample having a minimum amplitude signal; and
   positioning a range gate as a function of the first and second depths.

2. The method of claim 1, wherein the series of Doppler ultrasound pulses are alternately transmitted with B-mode imaging pulses.

3. The method of claim 2, wherein the echo signals are analyzed by calculating a first lag autocorrelation on echo signals received from the same depth in response to the series of Doppler pulses.

4. The method of claim 2, wherein the range gate is positioned at a depth having the minimum amplitude echo signal and the highest average velocity.

5. The method of claim 4, wherein the second depth is determined in response to the B-mode imaging pulses from a systole phase of a cardiac cycle.

6. An ultrasound imaging system comprising:
   an ultrasound transducer that transmits a series of ultrasound pulses into a tissue sample, and receives echo signals from the tissue sample in response to the series of ultrasound pulses;
   a beamformer that focuses the received echo signals;
   a B-mode processor that analyzes the focused echo signals to produce a B-mode image;
   a Doppler mode processor that analyzes the echo signals to produce a Doppler image; and a first processor that receives the echo signals and calculates an average velocity at a number of depths, the first processor determining a first depth of tissue having the highest average velocity; determining a second depth in the tissue sample having a minimum B-mode signal and instructing a processor in the ultrasound system to position a range gate as a function of the second depth and the first depth.

7. The system of claim 6, wherein the first processor operates in the background of the B-mode and Doppler processors.

8. A method of tracking a vessel in an ultrasound imaging system, comprising:

transmitting a series of Doppler ultrasound pulses into a tissue sample;

receiving echo signals along a number of receive beam lines and at a number of adjacent depths for each receive beam line in response to the series of Doppler ultrasound pluses transmitted;

analyzing the echo signals on each of the number of beam lines to determine the average velocity of the tissue at each of the number of adjacent depths; and positioning a range gate along the beam line at a depth having the highest average velocity.

9. The method of claim 8 wherein the number of beam lines lie in the same two dimensional plane.

10. The method of claim 8, wherein the number of beam lines lie in different planes in three dimensional space.

* * * * *